US00PP10938P

United States Patent [19]

McGredy

[11] Patent Number: Plant 10,938

[45] Date of Patent: Jun. 1, 1999

[54] HYBRID TEA ROSE PLANT NAMED 'MACOBORN'

[75] Inventor: Sam McGredy, Auckland, New Zealand

[73] Assignee: DeVor Nurseries, Inc., Watsonville, Calif.

[21] Appl. No.: 08/873,658

[22] Filed: Jun. 12, 1997

[51] Int. Cl.[6] ..... A01H 5/00

[52] U.S. Cl. ..... Plt./138

[58] Field of Search ..... Plt./18, 19, 20, Plt./11, 130, 137, 138, 139

[56] References Cited

U.S. PATENT DOCUMENTS

P.P. 3,226 7/1972 McGredy, IV ..... Plt./11

P.P. 3,640 10/1974 Kriloff ..... Plt./11

P.P. 4,855 6/1982 Bailey ..... Plt./11

P.P. 5,156 12/1983 Christensen ..... Plt./11

OTHER PUBLICATIONS

UPOV–ROM, Jan. 1998, Plant Variety Database, GTI Jouve Retrieval Software, 2citations for 'Macoborn'.

*Primary Examiner*—Howard J. Locker

*Attorney, Agent, or Firm*—Christie, Parker & Hale, LLP

[57] ABSTRACT

A hybrid tea rose plant variety producing flowers of multiple shades or tones of pink.

1 Drawing Sheet

BACKGROUND OF THE INVENTION

The present invention relates to a new and distinct hybrid tea rose variety which was originated by my crossing the variety known as 'Louise Gardner' as seed and the variety known as 'West Coast' as pollen parent. The varietal denomination of this new rose is 'Macoborn'.

SUMMARY OF THE INVENTION

Among the novel characteristics possessed by this new variety which distinguish it from its parents and all other varieties of which I am aware are its attractive bright colored flowers with slightly scalloped petals borne on a free flowering plant.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed to asexually reproduce the new variety.

COMPARISON WITH PARENTS

'Macoborn' flowers are of multiple pink shades or tones whereas 'Louise Gardner' flowers are a yellow red blend and 'West Coast' flowers are pink and the plant has more profuse foliage.

BRIEF DESCRIPTION OF ILLUSTRATION

The accompanying illustration shows a typical flower of the new variety depicted in color as nearly true as it is reasonably possible to make the same in a color illustration of this character.

DESCRIPTION OF THE NEW VARIETY

Parentage: Seedling.

*Seed parent.*—'Louise Gardner'.

*Pollen parent.*—'West Coast'.

Class: Hybrid tea.

The following is a detailed description of the new variety, from specimens grown in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

1. FLOWER

Blooming habit: Continuous.

A. Bud:

(1) *Size.*—Medium, about 2.7 to 3.25 cm long.

(2) *Form.*—Pointed.

(3) *Color.*—When sepals first divide, bud color is near 46A.

(4) *Sepals.*—Longer than bud, about 3 cm to 3.4 cm long, sepals divide and reflex when bloom opens; some sepals are foliaceous with leaf-shaped ends. Color: Near 144A.

(5) *Peduncle.*—Length: About 9 to 13.5 cm. Aspect: Small prickles. Strength: Erect, sturdy. Color: Near 144A.

(6) *Bracts.*—None.

B. Bloom:

(1) *Size.—Average size when fully expanded — about* 9.5 cm to 10.5 cm.

(2) *Borne.*—Singly.

(3) *Form.*—Imbricated, petals ruffled at edges and roll under.

(4) *Petalage.*—Number of petals under normal conditions — about 40 to 50.

(5) *Color (⅓ to ½ open).*—Outer petals: Outer edge near 50B with balance of petals near 48D, undersurface top edge near 50C with balance near 50D. Inner petals: Outer edge near 38B with balance of petals near 38C. Under surface — Most of petal is near 48D with base being near 46C. Base of petals — Near 7A. General tonality from a distance: multiple pink shades or tones.

(6) *Color (fully open)*.—Outer petals — Top surface: Top ⅓ of petal near 46D, center near 52D, base near 50D; Under surface: very tip near 54A, center near 55B, base near 157C. Inner petals — Top surface: top ⅔ of petal near 50A, bottom near 52C. Under surface: top edging near 55A, middle near 54B, bottom near 157C. Base of petals: Near 2B. General tonality from a distance: multiple pink shades or tones.

(7) *Color change*.—Bloom changes to a deeper pink color when exposed to the sun. Petal top surface: Near 50A. Petal under surface: Near 55A. Base of petals: Near 2B.

Petals:

(1) *Texture*.—Thick, smooth.
(2) *Appearance*.—Semi-velvety inside and outside.
(3) *Form*.—Elliptic.
(4) *Arrangement*.—Imbricated.
(5) *Petaloids*.—Few, 1 to 2.
(6) *Fragrance*.—Fruity.
(7) *Lasting quality*.—On plant about 10 to 14 days, after cutting about 7 to 9 days.
(8) *Persistence*.—Petals drop off cleanly.

2. REPRODUCTIVE ORGANS

A. Stamens:

(1) *Arrangement*.—Regularly arranged around styles.
(2) *Anthers*.—Near 22A.
(3) *Filaments*.—Near 1B.
(4) *Pollen*.—Near 22A.

B. Pistils:

(1) *Styles*.—Bunched, even length.
(2) *Stigmas*.—Near 11A.

C. Characteristics of hips: Not observed.

3. PLANT

A. Form: Upright, height about 150 to 250 cm and spread about 35 to 45 cm, in first season; flower stem length about 100 to 150 cm.

B. Growth: Vigorous.

C. Foliage: Compound 3 and 5 leaflets.

(1) *Size*.—Large, about 2.5 to 3 cm long, about 1.75 to 2.25 cm wide.
(2) *Quantity*.—Abundant.
(3) *Color*.—New foliage — upper side near 147A under side near 147B; mature foliage — upper side near 147A, under side near 147B.
(4) *Shape*.—Oval.
(5) *Texture*.—Upper side leathery and glossy; under side leathery, veiny.
(6) *Edge*.—Serrated.
(7) *Serration*.—Denticulate.
(8) *Stipules*.—Long with enlarged middle, slightly bearded, adnate, parallel, curls under, margins slightly bearded.
(9) *Rachis*.—Small prickles on under side.
(10) *Petioles*.—Top near 177A, under side near 146C.
(11) *Auricle*.—Long, incurved downward.
(12) *Resistance to disease*.—Good resistance to blackspot, mildew and rust.

D. Wood:

(1) *New wood*.—Near 166A, bark smooth.
(2) *Old wood*.—Near 144A, bark smooth.

E. Thorns:

(1) *Thorns*.—Quantity: On main stalk, profuse; laterals from stalk, many. Form: Wing-shaped base, curved downwardly. Length: About 1 to 1.4 cm long. Color: Near 183B with near 146C tip. Position: Irregular.
(2) *Prickles*.—Profuse.

G. Winter hardiness: Winter hardy in Watsonville, Calif.

I claim:

1. A new and distinct hybrid tea rose plant of the variety substantially as shown and described.

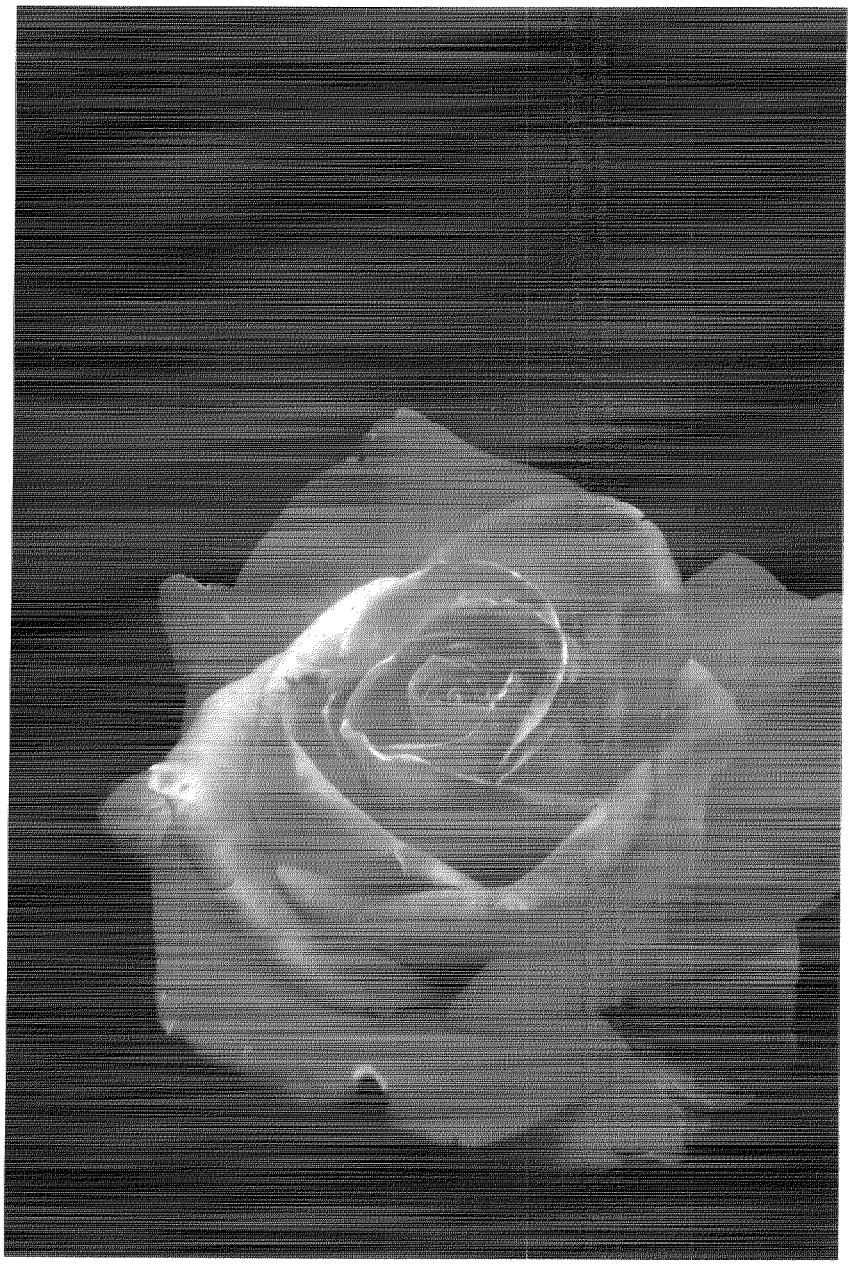

* * * * *